US007203704B1

(12) United States Patent
Stern et al.

(10) Patent No.: US 7,203,704 B1
(45) Date of Patent: Apr. 10, 2007

(54) METHOD AND APPARATUS OF CROSS-POLLINATING A POST TO COMPUTERIZED BULLETIN BOARDS

(75) Inventors: Douglas E. Stern, Waukesha, WI (US); Annebelle B. Crisostomo, Waukesha, WI (US); Christopher N. Japp, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 347 days.

(21) Appl. No.: 10/063,998

(22) Filed: Jun. 3, 2002

(51) Int. Cl.
*G06F 17/00* (2006.01)
*G06F 17/30* (2006.01)
*G06F 7/00* (2006.01)

(52) U.S. Cl. .................. 707/104.1; 707/5
(58) Field of Classification Search ............... 707/102, 707/104.1, 5
See application file for complete search history.

(56) References Cited

U.S. PATENT DOCUMENTS

| 5,799,151 | A * | 8/1998 | Hoffer ...................... 709/204 |
| 5,956,489 | A * | 9/1999 | San Andres et al. ........ 709/221 |
| 6,515,681 | B1 * | 2/2003 | Knight ....................... 715/751 |
| 6,594,673 | B1 * | 7/2003 | Smith et al. ............. 707/104.1 |
| 6,721,748 | B1 * | 4/2004 | Knight et al. ................ 707/10 |
| 7,007,226 | B1 * | 2/2006 | Smith et al. ................ 715/500 |
| 2001/0032252 | A1 * | 10/2001 | Durst et al. ................ 709/218 |
| 2001/0034639 | A1 * | 10/2001 | Jacoby et al. ................ 705/10 |
| 2002/0059526 | A1 * | 5/2002 | Dillon et al. ............... 713/201 |
| 2002/0062368 | A1 * | 5/2002 | Holtzman et al. .......... 709/224 |
| 2002/0138588 | A1 * | 9/2002 | Leeds ........................ 709/217 |
| 2003/0028441 | A1 * | 2/2003 | Barsness et al. ............. 705/26 |
| 2003/0163356 | A1 * | 8/2003 | Marks et al. .................. 705/7 |

* cited by examiner

*Primary Examiner*—Apu Motiz
*Assistant Examiner*—Cindy Nguyen
(74) *Attorney, Agent, or Firm*—Ziolkowski Patent Solutions Group, SC; Michael A. Della Penna; Carl B. Horton (57) ABSTRACT

A GUI such as a web page having a hyperlink thereon is provided and that allows a user to contribute a post to a bulletin board or a thread dedicated to a particular topic of interest. The present invention also includes a process by which the content of the user post is evaluated to determine if the post is relevant to other topics of interest to which other bulletin boards or threads are dedicated. If the user post is related to multiple topics of interest, then a copy of the post is automatically placed on each bulletin board or included in each thread to which the post relates. If a thread does not exist dedicated to a topic of interest, then a thread is automatically created.

22 Claims, 4 Drawing Sheets

METHOD AND APPARATUS OF CROSS-POLLINATING A POST TO COMPUTERIZED BULLETIN BOARDS

BACKGROUND OF INVENTION

The present invention relates generally to online computerized bulletin boards and, more particularly, to a method and apparatus for cross-pollinating postings across more than one computerized bulletin board.

Of the numerous uses of internet and web-based technology, one of the more widely used applications is the computerized bulletin board which provides an online forum for users to post comments regarding a particular topic of interest. Typically, a user accesses a graphical user interface (GUI) such as a website and accordingly navigates the website to find a GUI or window configured to enable a user post to a bulletin board. Some websites are specifically dedicated to "threads" of posts dedicated to a particular topic of interest. A user is able to view the messages in a particular thread and, if desirable, contribute a post to the thread.

Other known websites incorporate a hyperlink directly to a particular thread. For example, a website may include an article discussing a current event and also include a hyperlink to a thread that allows the reader to post comments regarding the article without having to navigate the website to find the bulletin board of user posts. Simply, the hyperlink automatically displays a window or page to facilitate user posting.

However, these websites are limited in that posts related to a particular topic of interest are not evaluated to determine if the post discusses or is relevant to another topic of interest to which another bulletin board or thread is dedicated. That is, a user post may relate to more than one topic of interest but, the post will only be included on the bulletin board where the user posts it. As such, a user may be required to navigate more than one bulletin board or thread of posts to view all the user posts directed or relevant to the particular topic of interest.

It is therefore desirable to design a method and apparatus in which postings to a particular bulletin board or thread are evaluated to determine other bulletin boards and/or threads to which a copy of the post should be placed.

BRIEF DESCRIPTION OF INVENTION

The present invention is directed to a method and apparatus for cross-pollinating postings across more than one computerized bulletin board. Specifically, a hyperlink is included on a GUI such as a web page that allows a user to contribute a post to a bulletin board or a thread dedicated to a particular topic of interest. The present invention however also includes a process by which the content of the user post is evaluated to determine if the post is relevant to other topics of interest to which other bulletin boards or threads are dedicated. If the user post is related to multiple topics of interest, then a copy of the post is automatically placed on each bulletin board or included in each thread to which the post relates. If a thread does not exist dedicated to a topic of interest, then a thread is automatically created.

In accordance with one aspect of the present invention, a method of cross-pollinating postings across more than one computerized bulletin board is provided. The method includes the steps of determining at least one topic of relevance of a post to a computerized bulletin board and determining one or more other computerized bulletin boards related to the at least one topic of relevance. The method also includes placing a copy of the post on each of the one or more other computerized bulletin boards related to the at least one topic of relevance.

The present invention may be carried out automatically according to a set of instructions of a computer program. Accordingly, in accordance with another aspect of the present invention, a computer readable storage medium having a computer program for content tagging posts to computerized bulletin boards is provided. The computer program represents a set of instructions that when executed by the computer causes the computer to detect a user post to a general computerized bulletin board and determine one or more specific topics of interest of the user post. The set of instructions further causes the computer to determine one or more specific computerized bulletin boards dedicated to the one or more specific topics of interest. The computer is then caused to place a copy of the user post on each of the one or more specific computerized bulletin boards.

In accordance with yet another aspect of the present invention, a computer data signal embodied in a carrier wave and representing a sequence of instructions which, when executed by at least one processor, causes the at least one processor to integrate a post with one or more computerized bulletin boards. The computer data signal causes the at least one processor to display a GUI having thereon one or more buttons wherein each button is associated with a topic of interest. The data signal then causes the processor to detect a user selection of a button and receive a post relevant to a topic of interest associated with the button selected. The at least one processor is then caused to place the post on a computerized bulletin board dedicated to the topic of interest as well as determine another topic of interest to which the post is relevant. The data signal then causes the computer to automatically place a copy of the post on another computer bulletin board related to the another topic of interest.

In accordance with yet another aspect of the present invention, a computerized system of network bulletin boards to facilitate discussion of a number of topics of interest includes a set of content-specific bulletin boards wherein each content-specific bulletin board is dedicated to a specific topic of interest. A content-general bulletin board is also provided and dedicated to a general topic of interest related to the specific topics of interest. The system further includes at least one graphical user and interface having a hyperlink thereon corresponding to at least one of the content-specific bulletin boards and the content-general bulletin board. The system also includes a computer having means to display at least one GUI and means to detect a user post associated with at least one topic of interest. The computer further includes a means to determine at least one of a specific topic of interest and a general topic of interest of the user post. The computer also includes means to automatically place a copy of the user post on each content-specific bulletin board to which the post relates and on the content-general bulletin board.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The present invention will be described with respect to cross-pollinating or content integrating bulletin boards dedicated to healthcare related topics. However, the present invention is equivalently applicable with any general area of interest outside the healthcare industry. The present invention facilitates the "seeding" of web conversation (both synchronous and asynchronous) and enhances the ability to analyze both web content for usefulness as well as a means for providing feedback regarding a particular product feature, news event, film review, etc. As will be described below, the present invention also includes a hyperlink placed on a GUI such as a web page that automatically directs the user, upon selection, to a web page that enables a user to comment on a particular topic of interest. Further, the present invention facilitates communication between members of an online community and provides a seeding for conversation wherein users particularly interested in a particular topic may further their knowledge and understanding of the topic by discussing the topic with other members of the online community. By cross-pollinating posts across multiple bulletin boards, communication between users is increased and enhanced.

Figure 1:
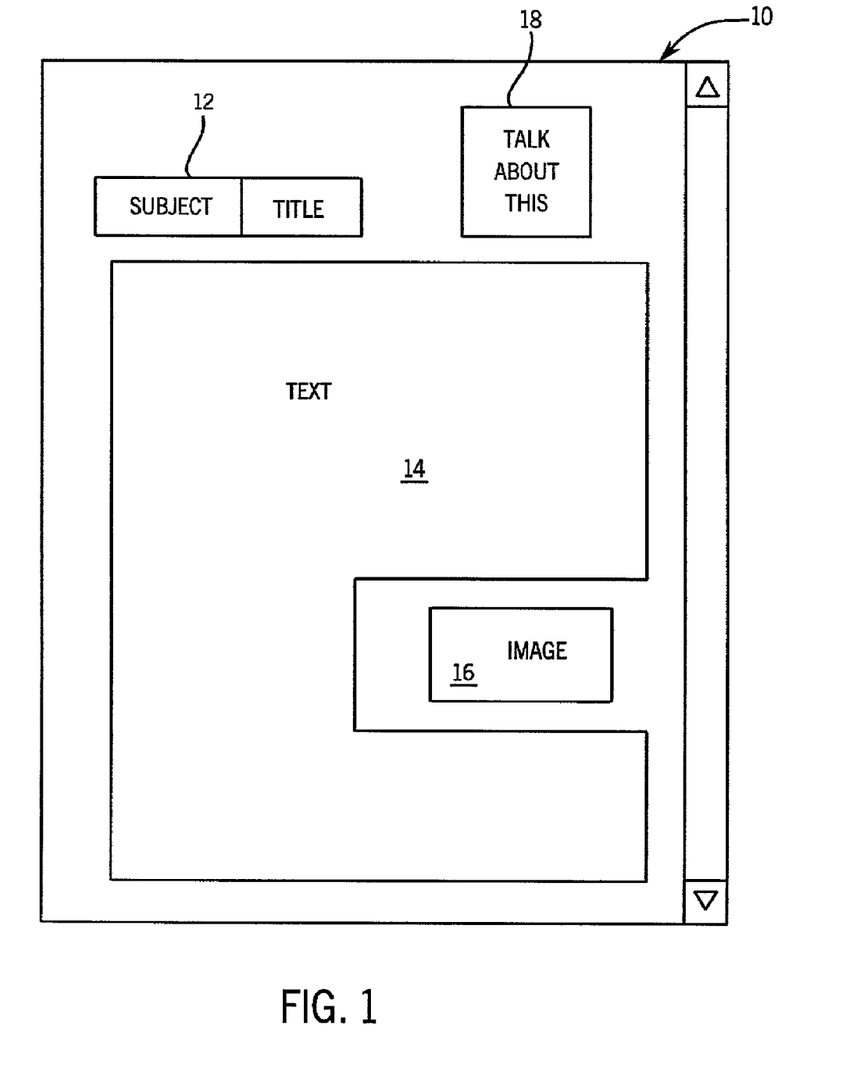
FIG. 1 is a representation of a GUI in accordance with one aspect of the present invention.

Referring now to FIG. 1, a GUI 10 which may be incorporated as a web page of a website is illustrated. GUI 10 illustrates one example of a web page incorporating an aspect of the present invention. GUIs 10 of any visual appearance are also contemplated. GUI 10 can include a subject and/or title field 12 identifying a subject or title of the web page. For example, for a healthcare related web page, a subject may identify a particular imaging modality such as magnetic resonance imaging, ultrasound, computer tomography, position emission tomography, etc. In another example, field 12 may include a title of an article, a film, etc. GUI 10 can further include a text area 14 which includes text related to the identified subject or title. GUI 10 may also include one or more images or elements of graphical art 16. A "TALK ABOUT THIS" button 18 is also provided. The "TALK ABOUT THIS" button 18, upon user selection, automatically causes a GUI to be displayed that facilitates user posting of comments relating to the subject and/or title.

Figure 2:
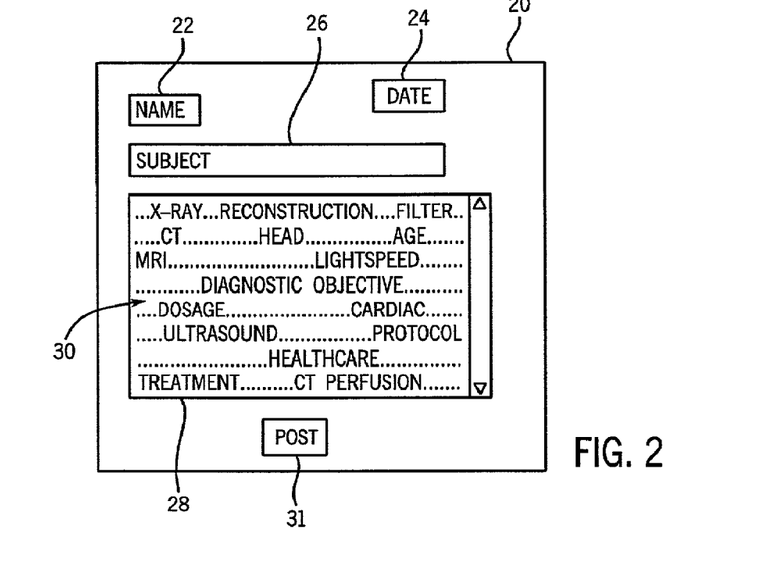
FIG. 2 is a representation of a GUI designed to facilitate a user post to a bulletin board or thread in accordance with the present invention.

Referring now to FIG. 2, GUI 20 is displayed upon user selection of button 18 of FIG. 1. GUI 20 allows the user to post comments directed to a particular topic of interest to a computerized bulletin board or thread. In placing a post directed to the topic of relevance, the user may input a name in field 22 and a date in field 24. Alternately, in an environment wherein the user must login, the name may automatically appear in field 22. Likewise, GUI 20 may be configured such that the date automatically appears in field 24. GUI 20 further includes a subject field 26 that allows the user to identify the particular topic of interest to which the comments are directed. In an alternate embodiment, the subject field 26 automatically reflects the subject and/or title in field box 12 of FIG. 1. GUI 20 also includes a text box 28 that allows the user to input commentary regarding the identified subject 26. The commentary 30 may include factual as well as opinion related information directed to the subject. As will be discussed shortly, the text of commentary 30 will be scanned and evaluated to determine keywords indicative of other topics of interest not specifically identified in field 26. Once the user has input commentary in field 28, user may select post button 31 to cause the post to be automatically placed on a computerized bulletin board or to a thread directed to the identified subject in field 26.

Figure 3:
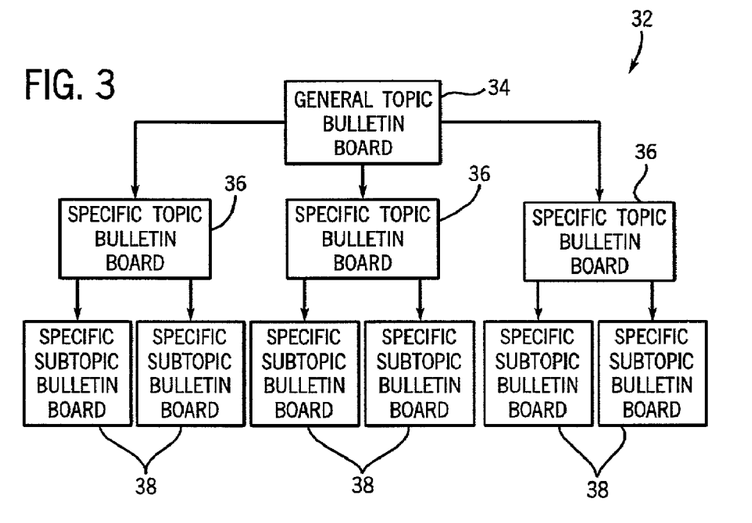
FIG. 3 is a schematic representation of a hierarchal bulletin board structure in accordance with one aspect of the present invention.

The present invention contemplates a hierarchal structure of computerized bulletin boards 32, an example of which is shown with reference to FIG. 3. That is, the present invention contemplates a user post to either a general topic bulletin board 34, a specific topic bulletin board 36, or a specific subtopic bulletin board 38. The user may or may not have knowledge that the post is directed to a general, specific, or specific subtopic bulletin board. The hierarchal structure of bulletin boards 32 allows for a free flow of information from a general topic to specific subtopics and vice versa. For example, a user post to a specific topic bulletin board 36 will also result, as will be described shortly, with a copy of the post being automatically placed on the general topic bulletin board 34. A post to a specific subtopic bulletin board 38 will not only result in a copy of the post being placed on a corresponding specific topic bulletin board 36 but a copy of the post will also be placed on the general topic bulletin board 34. This hierarchal structure 32 operates to insure that a post related to a particular subtopic may be found on the general topic bulletin board or a corresponding specific topic bulletin board 36 without requiring a user to navigate the entire hierarchal structure 32 to find the post to the specific subtopic bulletin board 38.

Figure 4:
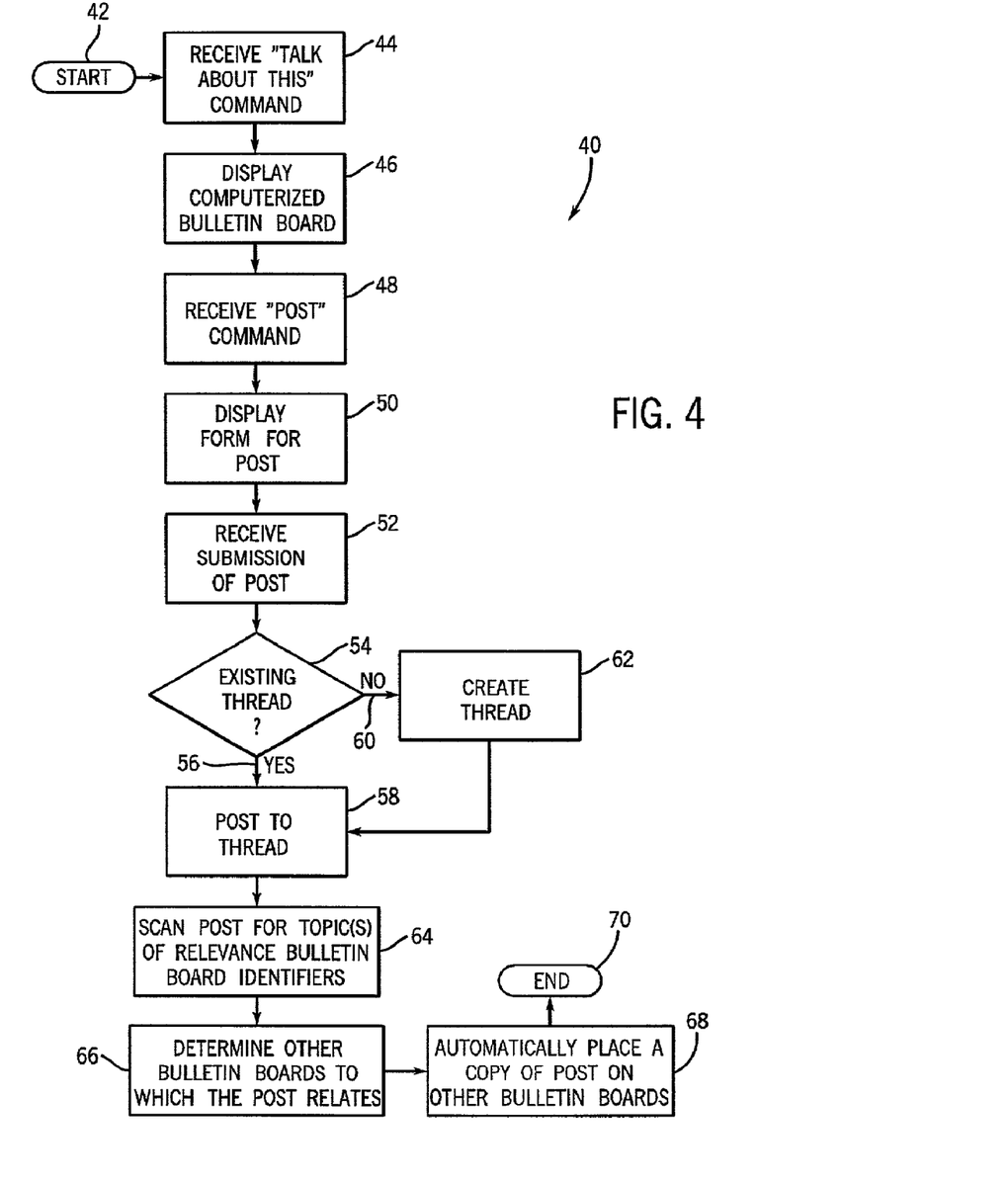
FIG. 4 is a flow chart setting forth the steps of a process for cross-pollinating postings across more than one computerized bulletin board in accordance with the present invention.

Referring now to FIG. 4, a technique 40 for cross-pollinating or content integrating postings across more than one computerized bulletin board is illustrated as a series of steps/acts that may be executed as a method and/or carried out by a set of instructions of a computer program or a sequence of instructions of a computer data signal embodied in a carrier wave. Technique 40 begins at 42 with the displaying of a GUI having a "TALK ABOUT THIS" button or hyperlink thereon, such as a GUI similar to that shown in FIG. 1. A "TALK ABOUT THIS" command is received at 44 indicative of a user's desire to post comments to a bulletin board or thread dedicated to the subject matter displayed on the GUI. Following reception of the "TALK ABOUT THIS" command at 44, a computerized bulletin board is displayed at 46. By displaying the computerized bulletin board, the user may either search and review the other posts to the bulletin board or thread or place a post to the bulletin board. At 48, a command to place a "post" is received. Responsive thereto, a form such as a GUI incorporated as a web page similar to that shown in FIG. 2 is displayed to the user 50. Accordingly, the user may complete the form including name, date, and subject information.

Once the user completes the form, technique 40 detects a submission of post command at 52. Once a command to submit the post is received at 52, technique 40 determines if there is an existing thread on the bulletin board dedicated to the identified topic of interest. If at 54 it is determined that an existing thread does exist 56, the post is automatically placed to the thread at 58. However, if there is not an existing thread 54, 60, a thread dedicated to the topic of interest is created at 62 and the post is then placed to the thread at 58.

After the user post is added to the thread or simultaneously therewith, the post is scanned and evaluated at 64 to determine other topics to which the user post is relevant. To determine the other topics of relevance, the text of the post is scanned for keywords or bulletin board identifiers. For example, in the context of healthcare related posts, the text of the post may be evaluated to determine if the post relates to a type of imaging modality, an exam type, a reconstruction process, hardware component, etc. Additionally, the post may also be scanned and evaluated to link a particular user to topics of relevance. That is, the computerized bulletin boards may be designed such that user posts are tracked based on authorship to determine a pattern of relevance such that subsequent posts by that author are automatically posted to bulletin boards related to the field of study of the author. Field of study information, etc. may be determined from a user profile that may be created. Additionally, an artificial intelligence or "smart" database may be implemented having data stored thereon setting forth a relationship between synonyms or other terms. That is, the technique may include a function wherein the identified keywords are evaluated to determine related terms. Determining those terms that relate to the identified keywords may be obtained by accessing the "smart" database. As a result, computerized bulletin boards related or dedicated to terms synonymous with or related to the keywords may also be identified so that a copy of the post may be placed to those boards as well.

By scanning for keywords or bulletin board identifiers, the technique 40 is able to determine other bulletin boards to which the post relates at 66. A search engine or "web crawler" may be activated to determine the other bulletin boards. That is, for a computerized network of bulletin boards incorporating the hierarchal structure shown in FIG. 3, the technique 40 may determine at 66 if a copy of the user post should be placed in a thread on a specific topic bulletin board or a general topic bulletin board. Once the other bulletin boards to which the post relates are properly identified, technique 40 automatically places a copy of the post on the other bulletin boards at 68. If placement of the copy of the post on the other bulletin boards requires a new thread dedicated to the topic of interest be created, technique 40 automatically does so. After the copies are automatically placed on the one or more other bulletin boards, the technique ends at 70.

Figure 5:
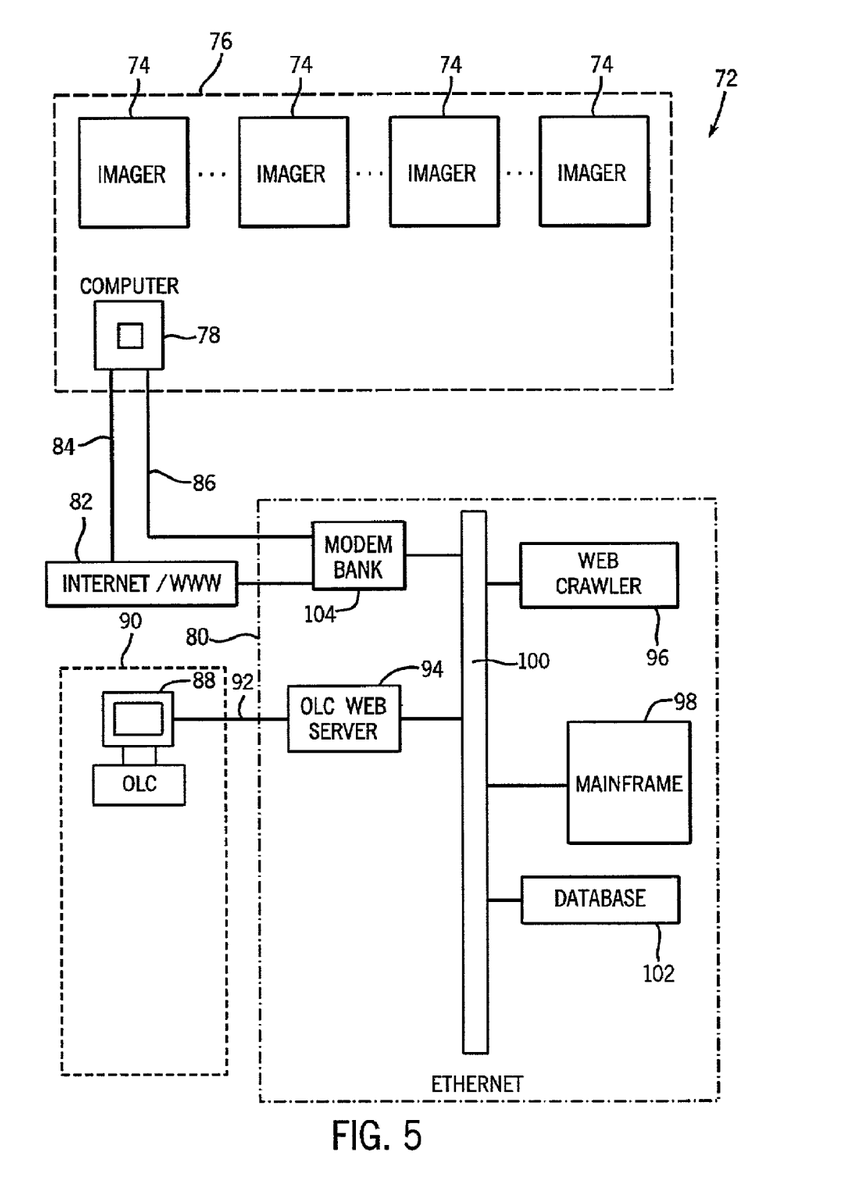
FIG. 5 is a block diagram of a system for which the present invention is implemented therein.

Referring to FIG. 5, an overview block diagram of a medical diagnostic and service system 72 is shown which may include a plurality of medical devices 74. The plurality of medical diagnostic devices 74 can include a variety of medical diagnostic systems of various modalities. For example, the plurality of medical diagnostics devices can include magnetic resonance imaging (MRI) systems, ultrasound systems, x-ray systems, computed tomography (CT) systems, as well as, positron emission tomography (PET) systems, or any other type of medical imaging system. The plurality of diagnostic devices may be centrally located or remotely located from one another in a medical treatment facility 76 such as a hospital.

Hospital 76 further includes a plurality of user workstations 78 to, among other tasks, facilitate user posting to a website or computerized bulletin board. Computer workstations 78 allow a user to communicate with a centralized facility 80 remote from the treatment facility 76. As heretofore discussed, this communication between the user and the centralized facility 80 via computer workstations 78 enable the user to post a comment to a computerized bulletin board or website. Each computer workstation 78 includes an internal modem to connect the workstation 78 to a communications link, such as the Internet 82, through link 84 to communicate with the centralized facility 80. Alternatively, computer workstation 78 may be directly connected to the centralized facility 80 via link 86 which can include a dedicated line or an Internet link. As previously discussed, the user may access a graphical user interface via links 84 or 86 to post the comments or view comments by other users to the computerized bulletin board.

Each workstation 78 described herein may be linked selectively to the centralized facility. According to the present invention, any acceptable network may be employed whether public, open, dedicated, private, or so forth. The communications links to the network may be of any acceptable type, including conventional telephone lines, fiber optic, cable modem links, digital subscriber lines, wireless data transfer systems, or the like. Each of the systems is provided with communications interface hardware and software of generally known design, permitting each to establish network link and exchange data with the centralized facility 80. In some cases, during period when no data is exchanged between the workstation and the centralized facility, the network connection is terminated. In other cases, the network connection is maintained continuously.

In a further embodiment, a user may access the computerized bulletin boards from a computer or workstation 88 in a remote link 90 remote from the medical treatment facility 74, which can be a part of the centralized facility 80, or be separately connected to the centralized facility 80 by a dialup link 92 to a web server 94 in the centralized facility 80.

The centralized facility 80 includes a number of processing systems including computers for supporting the computerized bulletin boards and graphical user interfaces of a website. A "web crawler" or search engine 96 is also supported. Other processor systems include a main frame 98. Each is connectable and can transmit data through a network, such as an Ethernet 100 with one another, and/or with at least one database 102. However, it is understood that the single representation of a database in FIG. 5 is for demonstrative purposes only, and it is assumed that there is a need for multiple databases in such a system. The at least one database may also include a "smart" database that supports the artificial intelligence heretofore described. A bank of modems 104 is connected to the Ethernet 100 to relay data from the centralized facility 80 to the remote customer workstation.

Accordingly, the present invention includes a method of cross-pollinating postings across more than one computerized bulletin board. The method includes the step of determining at least one topic of relevance of a post to a computerized bulletin board as well as determining one or more other computerized bulletin boards related to the at least one topic of relevance. The method further includes placing a copy of the post on each of the one or more other computerized bulletin boards related to at least one topic of relevance. The method further includes a step of searching the post for one or more keywords indicative of at least one topic of relevance as well as matching the one or more keywords with one or more computerized bulletin board topic identifiers to determine an appropriate computerized bulletin board to place a copy of the post. A hierarchal structure of bulletin boards is contemplated having bulletin boards directed to general topics of relevance as well as bulletin boards related to specific topics of relevance. The method further includes the step of scanning the text of the post to determine general topics of relevance for which the post relates as well as determining specific topics of relevance to which the post relates. Thereafter, a copy of the post is placed on each general topic bulletin board and each specific topic bulletin board to which the post relates. Furthermore, the method determines if the post relates to a previous thread of posts and if so automatically placing the post in the thread. If a thread directed to the topic of interest to which the post relates does not exist, the method automatically creates a new thread and places the post in the thread.

A computer readable storage medium having a computer program for content tagging posts to computerized bulletin boards is also provided. The computer program represents a set of instructions that when executed by computer causes the computer to detect a user post to a general computerized bulletin board as well as determine one or more specific topics of relevance of the user post. The computer program also causes the computer to determine one or more specific computerized bulletin boards dedicated to the one or more specific topics of relevance and further causes the computer to place a copy of the user post on each of the one or more specific computerized bulletin boards. The set of instructions further causes the computer to search the user post for one or more keywords indicative of a one or more specific topics of relevance to which the user post refers and scan the text, a subject identifier, or an author identifier to determine the one or more specific topics of relevance. The computer is then caused to automatically place the user post in the thread dedicated to the specific topic of relevance on the one or more specific computerized bulletin boards. The set of instructions further causes the computer to automatically generate a new thread on a specific computerized bulletin board dedicated to a specific topic of relevance if a thread on a bulletin board does not currently exist.

In a further embodiment of the present invention, the computer data signal embodied in a carrier wave and representing a sequence of instructions which, when executed by at least one processor, causes the at least one processor to integrate a post with one or more computerized bulletin boards is provided. The computer data signal causes a graphical user interface to be displayed having thereon one or more buttons dedicated to a topic of interest. The computer data signal causes the processor to detect a user selection of a button and receive a post relevant to a topic of interest associated with the button selected. The computer data signal then causes the processor to place the post on a computerized bulletin board dedicated to the topic of interest as well as determine another topic of interest to which the post is relevant. The processor then automatically places a copy of the post on another computerized bulletin board related to the another topic of interest. Further, the processor determines at least one subtopic of interest of the user post and assigns the post to a thread of previous posts discussing the subtopic of interest. Alternately, the computer data signal causes the processor to generate a new thread of discussion related to the subtopic of interest if there is not an existing thread of discussion dedicated to the subtopic of interest. Further, the computer data signal causes the processor to detect a user post directly to computerized bulletin board dedicated to a topic of interest and automatically place a copy of the user post directly to another computerized bulletin board dedicated to another topic of interest to which the user post relates. The computer data signal also causes the processor to detect a user post directly to a computerized bulletin board dedicated to a subtopic of interest and automatically place a copy of the user post directly on a computerized bulletin board dedicated to a general topic of interest encompassing the specific topic of interest to which the user post relates.

Accordingly, a computerized system of network bulletin boards to facilitate discussion of a number of topics of interest is contemplated. The system includes a set of content-specific bulletin boards wherein each content-specific bulletin board is dedicated to a specific topic of interest. A content-general bulletin board is also provided and dedicated to a general topic of interest related to the specific topic of interest. The computerized system also contemplates at least one GUI having a hyperlink thereon corresponding to at least of the content-specific bulletin boards and the content-general bulletin board. A computer is also provided having means to display at least one GUI and means to detect a user post associated with the at least one topic of interest. The computer also has means to determine at least one specific topic of interest and a general topic of interest of the user post. The computer further includes means to automatically place a copy of the user post on each content-specific bulletin board to which the post relates and on the content-general bulletin board.

While the present invention has been described with respect to the online discussion of healthcare related topics and users located within a medical treatment facility, the present invention is equivalently applicable with the discussion of other topics of interest including those outside healthcare or healthcare related industries. The present invention may be implemented for bulletin boards of any topic of interest to facilitate online communication and discussion with respect to any topic of interest. Additionally, the present invention is applicable for users of workstation remote from a centralized processing facility including portable computers, laptops, PDAs, and the like.

The present invention has been described in terms of the preferred embodiment, and it is recognized that equivalents, alternatives, and modifications, aside from those expressly stated, are possible and within the scope of the appending claims.

What is claimed is:

1. A method of cross-pollinating postings across more than one computerized bulletin board comprising the steps of:
    detecting a post having a body and a subject header to a computerized bulletin board;
    automatically determining at least one topic of relevance from the body of the post to the computerized bulletin board;
    automatically determining one or more other computerized bulletin boards related to the at least one topic of relevance; and
    automatically placing a copy of the post on each of the one or more other computerized bulletin boards related to the at least one topic of relevance.

2. The method of claim 1 further comprising the step of automatically searching the body of the post for one or more keywords indicative of the at least one topic of relevance.

3. The method of claim 2 further comprising the step of accessing a smart database and determining therefrom terms related to the one or more keywords.

4. The method of claim 2 further comprising the step of matching the one or more keywords with one or more computerized bulletin board topic identifiers to determine an appropriate computerized bulletin board to place a copy of the post.

5. The method of claim 1 wherein the computerized bulletin board is related to general topics of relevance and the one or more other computerized bulletin boards are related to specific topics of relevance.

6. The method of claim 5 further comprising the step of scanning text of the body of the post to the computerized bulletin board related to general topics of relevance for keywords referencing one or more specific topics of relevance and automatically placing a copy of the post on each of the one or more other computerized bulletin boards related to the one or more specific topics of relevance.

7. The method of claim 6 further comprising the step of automatically placing a copy of a post to a computerized bulletin board related to a specific topic of relevance on the computerized bulletin board dedicated to general topics of relevance.

8. The method of claim 1 further comprising the step of determining if the post relates to a thread of previous posts on the computerized bulletin board and, if so, automatically placing the post in the thread.

9. The method of claim 8 further comprising the step of automatically creating a new thread on the computerized bulletin board related to the at least one topic of relevance.

10. A computer readable storage medium having a computer program for content tagging posts to computerized bulletin boards and representing a set of instructions that when executed by a computer causes the computer to:
   detect a user post to a general computerized bulletin board, the post having a subject identifier and a commentary;
   determine one or more specific topics of relevance of the user post from text of the commentary of the user post;
   determine one or more specific computerized bulletin boards dedicated to the one or more specific topics of relevance; and
   place a copy of the user post on each of the one or more specific computerized bulletin boards.

11. The computer readable storage medium of claim 10 wherein the set of instructions further causes the computer to search the text of the commentary of the user post for one or more keywords indicative of the one or more specific topics of relevance to which the user post refers.

12. The computer readable storage medium of claim 11 wherein the set of instructions further causes the computer to scan at least text in the subject identifier and text in the commentary of the user post to find the one or more keywords indicative of the one or more specific topics of relevance.

13. The computer readable storage medium of claim 10 wherein the set of instructions further causes the computer to determine an author of the post and based on the determined author place a copy of the post to one or more specific computerized bulletin boards dedicated to one or more fields of interest of the author.

14. The computer readable storage medium of claim 13 wherein the set of instructions further causes the computer to determine the one or more fields of interest of the author from a look-up table containing data correlating author information with field-of-interest information.

15. The computer readable storage medium of claim 10 wherein the set of instructions further causes the computer to automatically place the user post in a thread dedicated to a specific topic of relevance on the one or more specific computerized bulletin boards.

16. The computer readable storage medium of claim 10 wherein the set of instructions further causes the computer to automatically generate a new thread on a specific computerized bulletin board dedicated to a specific topic of relevance of the user post.

17. A computer readable storage medium having a set of instructions which, when executed by at least one processor, causes the at least one processor to integrate a post with one or more computerized bulletin boards by:
   displaying a GUI having thereon one or more buttons, wherein each button is associated with a topic of interest;
   detecting a user selection era button;
   reeeiving a post having a subject identifier and a body relevant to a topic of interest associated with the button selected;
   placing the post on a computerized bulletin board dedicated to the topic of interest;
   scanning the body of the post and determining another topic of interest to which the post is relevant; and
   automatically placing a copy of the post on another computerized bulletin board related to the another topic of interest.

18. The computer data signal of claim 17 further causing the act of determining at least one subtopic of interest of the user post.

19. The computer data signal of claim 18 further causing the act of assigning the post to a thread of previous posts discussing a subtopic of interest.

20. The computer data signal of claim 18 further causing the act of generating a new thread of discussion related to a subtopic of interest if there is not an existing thread of discussion dedicated to the subtopic of interest.

21. The computer data signal of claim 17 further causing the acts of detecting a user post directly to a computerized bulletin board dedicated to a topic of interest and automatically placing a copy of the user post directly to another computerized bulletin board dedicated to another topic of interest to which the user post directly to the computerized bulletin board relates.

22. A computerized system of networked bulletin boards to facilitate discussion of a number of topics of interest comprising:
   a set of content-specific bulletin boards wherein each content-specific bulletin board is dedicated to a specific topic of interest;
   a content-general bulletin board dedicated to a general topic interest related to the specific topics of interest;
   at least one GUI having a hyperlink thereon corresponding to at least one of the content-specific bulletin boards and the content-general bulletin board; and
   a computer having:
      means to display the at least one GUI;
      means to detect a user post associated with at least one topic of interest;
      means to determine at least one of a specific topic of interest and a general topic of interest of the user post; and
      means to automatically place a copy of the user post on each content-specific bulletin board to which the post relates and on the content-general bulletin board without copying all other user posts of the set of content-specific bulletin boards.

* * * * *

UNITED STATES PATENT AND TRADEMARK OFFICE
CERTIFICATE OF CORRECTION

PATENT NO. : 7,203,704 B1 Page 1 of 1
APPLICATION NO. : 10/063998
DATED : April 10, 2007
INVENTOR(S) : Stern et al.

It is certified that error appears in the above-identified patent and that said Letters Patent is hereby corrected as shown below:

Col. 10, line 12 (Claim 17), delete "reeeiving" and substitute therefore -- receiving --.

Signed and Sealed this

Tenth Day of July, 2007

JON W. DUDAS
*Director of the United States Patent and Trademark Office*